United States Patent
Li et al.

(10) Patent No.: US 9,392,764 B1
(45) Date of Patent: Jul. 19, 2016

(54) SOYBEAN VARIETY 'G12PR-63R2'

(71) Applicant: University of Georgia Research Foundation, Inc., Athens, GA (US)

(72) Inventors: Zenglu Li, Athens, GA (US); Edwin D. Wood, Winterville, GA (US); H. Roger Boerma, Athens, GA (US); James W. Buck, Fayetteville, GA (US); James P. Noe, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/833,353

(22) Filed: Aug. 24, 2015

(51) Int. Cl.
| | |
|---|---|
| *A01H 5/10* | (2006.01) |
| *A01H 5/00* | (2006.01) |
| *A01H 1/02* | (2006.01) |
| *A01H 4/00* | (2006.01) |
| *C12N 15/82* | (2006.01) |
| *C12N 5/04* | (2006.01) |
| *C12N 15/54* | (2006.01) |
| *C12N 15/32* | (2006.01) |
| *C07K 14/415* | (2006.01) |

(52) U.S. Cl.
CPC .. *A01H 5/10* (2013.01); *A01H 1/02* (2013.01); *A01H 4/00* (2013.01); *C07K 14/415* (2013.01); *C12N 5/04* (2013.01); *C12N 15/8218* (2013.01); *C12N 15/8241* (2013.01); *C12N 15/8243* (2013.01); *C12N 15/8245* (2013.01); *C12N 15/8247* (2013.01); *C12N 15/8251* (2013.01); *C12N 15/8271* (2013.01); *C12N 15/8273* (2013.01); *C12N 15/8274* (2013.01); *C12N 15/8275* (2013.01); *C12N 15/8277* (2013.01); *C12N 15/8278* (2013.01); *C12N 15/8279* (2013.01); *C12N 15/8281* (2013.01); *C12N 15/8282* (2013.01); *C12N 15/8283* (2013.01); *C12N 15/8285* (2013.01); *C12N 15/8286* (2013.01); *C12N 15/8289* (2013.01)

(58) Field of Classification Search
None
See application file for complete search history.

(56) References Cited

U.S. PATENT DOCUMENTS 7,161,066 B2 * 1/2007 Tinius .................. A01H 5/10
435/415

OTHER PUBLICATIONS

Fehr (Iowa State University, "Principles of Cultivar Development," vol. 1 Theory and Technique and vol. 2 Crop Species, Soybean, Macmillan Publishing Company, New York, pp. 360-376, 1987) a.*
Haun et al (Plant Physiology, Feb. 2011, vol. 155, pp. 645-655).*

* cited by examiner

*Primary Examiner* — Lee V Visone
(74) *Attorney, Agent, or Firm* — Klarquist Sparkman, LLP

(57) ABSTRACT

Herein provided is a new soybean variety designated 'G12PR-63R2' as well as the seeds, plants and derivatives of the new soybean variety 'G12PR-63R2'. Also provided are tissue cultures of the new soybean variety 'G12PR-63R2' and the plants regenerated therefrom. Methods for producing soybean plants by crossing the new soybean variety 'G12PR-63R2' with itself or another soybean variety and plants produced by such methods are also provided.

27 Claims, No Drawings

SOYBEAN VARIETY 'G12PR-63R2'

FIELD

This disclosure provides a new and distinctive soybean variety, 'G12PR-63R2'.

BACKGROUND

Soybean (*Glycine max*), is an important and valuable field crop. The USDA Crop Reporting Service has reported that over 93% of U.S. soybean acreage was planted Roundup® Ready soybean cultivars in 2013. In the southeastern USA soybean growers prefer maturity group (MG) VII or MG VIII soybean cultivars. Plant breeders continually develop stable, high yielding soybean varieties that are agronomically sound, for example to maximize the amount of grain produced on the land used and to supply food for both animals and humans. To accomplish this goal, soybean breeders select and develop soybean plants having one or more desired traits that result in superior varieties. Exemplary desired traits include higher seed yield, resistance to diseases and insects, better stems and roots, tolerance to drought and heat, better agronomic quality, resistance to herbicides, and improvements in compositional traits.

SUMMARY

The present disclosure relates to a new soybean variety, 'G12PR-63R2'. This new variety is an early MG VII (Relative Maturity 7.3), glyphosate tolerant line with resistance to Southern root-knot nematode, Peanut root-knot nematode, Javanese root-knot nematode, and race 3 of the soybean cyst nematode, and in some examples improved seed yield relative to other glyphosate tolerant soybeans. Exemplary commonly grown MG VII cultivars include 'G00-3880', 'AG7733', 'P97M50', 'AG7934', 'AG7231', 'AG7532' and 'AG7333'. G12PR-63R2 exceeded the yield of Roundup ready cultivar 'P07M50' by 2.7% (1.5 bu/a) in 10 environments and has similar yield as RR2Y cultivars, 'AG7733' and 'AG7934' across 8 to 10 environments (Table 5). Thus, the new variety is adapted to areas of the United States (such as the southern and southeastern United States) that commonly grow MG VII soybean cultivars and to areas that are known to have or expected to have damaging levels of the Southern root-knot nematode, Peanut root-knot nematode, Javanese root-knot nematode, and/or race 3 of the soybean cyst nematode.

A deposit of the new soybean variety 'G12PR-63R2' will be made with the American Type Culture Collection (ATCC), 10801 University Blvd., Manassas, Va., 20110. The date of deposit is Sep. 9, 2015. The deposit is intended to meet all of the requirements of 37 C.F.R. §§1.801-1.809. The accession number for those deposited seeds of the new soybean variety 'G12PR-63R2' is ATCC Accession No. PTA-122508. The deposit will be maintained in the depository for a period of 30 years, or 5 years after the last request, or for the effective life of the patent, whichever is longer, and will be replaced if necessary during that period. In one embodiment, the disclosure provides soybean seed deposited as ATCC Accession No. PTA-122508, as well as bulk soybean seed containing such seeds. The plant rows selected to create the initial breeder seed of 'G12PR-63R2' were all uniformly resistant to glyphosate at the labeled rates for Roundup® Ready soybeans. All seed increases of 'G12PR-63R2' received an application of herbicidal rates of the Roundup® herbicide.

The disclosure provides soybean plants having or consisting of the morphological and physiological characteristics of 'G12PR-63R2', such as the characteristics noted in Tables 1-7, for example resistance to root-knot nematodes (such as Southern, Peanut, and/or Javanese root-knot nematodes), and/or to soybean cyst nematode (such as race 3 of the soybean cyst nematode). Also provided are seeds of such plants, progeny of such plants, parts of such plants (such as pollen, ovules and cells). In one example, the disclosure provides soybean plants having the genotype of 'G12PR-63R2'. For example, the disclosure provides plants produced by growing the seed of the new soybean variety 'G12PR-63R2'.

The disclosure provides a tissue culture of regenerable cells of the new soybean variety 'G12PR-63R2', as well as plants regenerated therefrom. Such regenerated soybean plants can include or consist of the physiological and morphological characteristics of a plant grown from the seed of the new soybean variety 'G12PR-63R2'. Exemplary regenerable cells include but are not limited to those from protoplasts or cells, such as those from embryos, meristematic cells, pollen, leaves, roots, root tips, anther, pistil, flower, seed, cotyledon, hypocotyl, shoot, or stem of the new soybean variety 'G12PR-63R2'.

Methods of producing soybean seed from the 'G12PR-63R2' soybean plants are provided. In some examples such methods include crossing 'G12PR-63R2' with itself or a second soybean plant and harvesting a resulting soybean seed. In some examples, the second soybean plant has one or more desirable traits, which is/are introduced into plants and seeds resulting from such a cross. For example, the second plant can be transgenic, wherein the transgene confers the desirable trait(s). Seeds produced by such methods, including $F_1$ hybrid seeds, as well as soybean plants or parts thereof produced by growing such a seed, are provided. In some examples, the method of crossing includes planting seeds of the new soybean variety 'G12PR-63R2', cultivating soybean plants resulting from the seeds until the plants bear flowers, allowing fertilization of the flowers of the plants; and harvesting seeds produced from the plants.

Methods are provided for producing a plant of soybean variety 'G12PR-63R2' that has one or more added desired traits, as well as plants and seeds generated from such methods. In one example, such a method provides a soybean plant having a single locus conversion of the new soybean variety 'G12PR-63R2', wherein the soybean plant includes or expresses the physiological and morphological characteristics of the new soybean variety 'G12PR-63R2' (such as those shown in Tables 1-7, such as Table 6). In some embodiments, the single locus conversion can include a dominant or recessive allele. Such methods can include introducing a transgene that confers one or more desired traits into a plant of the new soybean variety 'G12PR-63R2'. Exemplary desired traits include herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance (such as tolerance to drought, heat, cold, low or high soil pH level, and/or salt); modified phosphorus characteristics, modified antioxidant characteristics, modified essential seed amino acid characteristics, modified fatty acid metabolism, modified carbohydrate metabolism, modified soybean fiber characteristics or other improved nutritional qualities.

Methods of introducing a single locus conversion (such as a desired trait) into the new soybean variety 'G12PR-63R2' are provided. In some examples the methods include (a) crossing a plant of variety 'G12PR-63R2' with a second plant having one or more desired traits to produce $F_1$ progeny plants; (b) selecting $F_1$ progeny plants that have the desired trait to produce selected $F_1$ progeny plants; (c) crossing the selected progeny plants with at least a first plant of variety 'G12PR-63R2' to produce backcross progeny plants; (d) selecting backcross progeny plants that have the desired trait and physiological and morphological characteristics of soybean variety 'G12PR-63R2' to produce selected backcross progeny plants; and (e) repeating steps (c) and (d) one or more times in succession to produce selected second or higher backcross progeny plants that include the desired trait and the physiological and morphological characteristics of soybean variety 'G12PR-63R2' when grown in the same environmental conditions. In some embodiments, the single locus confers a desirable trait, such as herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance (such as tolerance to drought, heat, low or high soil pH level, and/or salt), modified phosphorus characteristics, modified antioxidant characteristics, modified essential seed amino acid characteristics, modified fatty acid metabolism, modified carbohydrate metabolism, and modified soybean fiber characteristics. In some examples, the single locus confers the ability to synthesize a protein encoded by a gene located within the single locus.

Methods of producing a soybean plant derived from the new soybean variety 'G12PR-63R2', such as an inbred soybean plant, are provided. In particular examples the method includes (a) preparing a progeny plant derived from the new soybean variety 'G12PR-63R2' by crossing a plant of 'G12PR-63R2' with a soybean plant of a second variety; and (b) crossing the progeny plant with itself or a second plant to produce a progeny plant of a subsequent generation which is derived from a plant of the new soybean variety 'G12PR-63R2'. In some embodiments, the method further includes (c) growing a progeny plant of a subsequent generation from said seed and crossing the progeny plant of a subsequent generation with itself or a second plant; and (d) repeating steps (b) and (c) for at least 2 additional generations (such as at least 3, at least 5, or at least 10 additional generations, such as 2, 3, 4, 5, 6, 7, 8, 9, 10, 11, 12, 13, 14, 15, 16, 17, 18, 19 or 20 additional generations) with sufficient inbreeding to produce an inbred soybean plant derived from the new soybean variety 'G12PR-63R2'. In other examples, the method includes (a) crossing a soybean plant derived from the new soybean variety 'G12PR-63R2' with itself or another soybean plant to yield additional soybean variety 'G12PR-63R2'-derived progeny soybean seed; (b) growing the progeny soybean seed of (a) under plant growth conditions, to yield additional soybean variety 'G12PR-63R2'-derived soybean plants; and (c) repeating the crossing and growing steps of (a) and (b) from 0 to 7 times (such as 0 to 4 or 1 to 5 times, such as 0, 1, 2, 3, 4, 5, 6, or 7 times) to generate further soybean variety 'G12PR-63R2'-derived soybean plants.

Methods are provided for developing a new soybean plant using the new 'G12PR-63R2' variety. For example, the methods can include using 'G12PR-63R2' plants or parts thereof as a source of breeding material in plant breeding techniques, such as recurrent selection, mass selection, bulk selection, backcrossing, pedigree breeding, genetic marker-assisted selection and genetic transformation. In some examples, a plant of the new soybean variety 'G12PR-63R2' is used as the male or female parent.

The disclosure provides a first generation ($F_1$) hybrid soybean seed produced by crossing a plant of the new soybean variety 'G12PR-63R2' to a second soybean plant. In some embodiments, the $F_1$ hybrid soybean plant is grown from the hybrid seed produced by crossing the new soybean variety 'G12PR-63R2' to a second soybean plant. In specific examples, provided is a seed of an $F_1$ hybrid plant produced with the new soybean variety 'G12PR-63R2' as one parent, the second generation ($F_2$) hybrid soybean plant grown from the seed of the $F_1$ hybrid plant, and the seeds of the $F_2$ hybrid plant.

Methods of producing hybrid soybean seeds are also provided. In one example the method includes crossing the new soybean variety 'G12PR-63R2' to a second, distinct soybean plant which is nonisogenic to the new soybean variety 'G12PR-63R2'. In some examples, the method includes cultivating soybean plants grown from seeds of the new soybean variety 'G12PR-63R2' and cultivating soybean plants grown from seeds of a second, distinct soybean plant, until the plants bear flowers. A flower on one of the two plants is cross pollinated with the pollen of the other plant, and the seeds resulting from such a cross are harvested.

The disclosure also provides soybean plants and parts thereof produced by any of the methods disclosed herein. Thus, provided herein are plants of soybean variety 'G12PR-63R2' that further include a single locus conversion, such as one or more desired traits, for example produced by backcrossing or genetic transformation. In some embodiments, the soybean plants produced by the disclosed methods includes at least two, at least three, at least four, at least five, or at least 10 of the traits of the new soybean variety 'G12PR-63R2' as described herein. In some embodiments, the soybean plants produced by the disclosed methods include at least two, at least three, at least four, at least five, or at least 10 of the traits of the new soybean variety 'G12PR-63R2' (see Tables 1-7), such as 2, 3, 4, 5, 6 or all 7 of early maturity, glyphosate tolerance, increased seed production, resistance to Southern root-knot nematodes, resistance to Peanut root-knot nematode, resistance to Javanese root-knot nematodes, and resistance to race 3 of soybean cyst nematode, as described herein.

Methods of producing a commodity plant product are provided. In some examples the method includes obtaining or supplying a plant of the new soybean variety 'G12PR-63R2', or a part thereof, and producing the commodity plant product therefrom. In some examples the method includes growing and harvesting the plant, or a part thereof. Exemplary commodity plant products include but are not limited to a protein concentrate, a protein isolate, soybean hulls, meal, flour or oil.

The foregoing and other objects and features of the disclosure will become more apparent from the following detailed description.

DETAILED DESCRIPTION

Description of Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Cell. Cell as used herein includes a plant cell, whether isolated, in tissue culture or incorporated in a plant or plant part.

Cross. Synonymous with hybridize or crossbreed. Includes the mating of genetically different individual plants, such as the mating of two parent plants.

Cross-pollination: Fertilization by the union of two gametes from different plants.

$F_1$ hybrid: The first generation progeny of the cross of two nonisogenic plants. Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Javanese Root-knot Nematode: A plant pathogenic nematode (*Meloidogyne javanica*) that attacks the roots of its host plant. Resistance or sensitivity to Javanese root-knot nematodes is based on a disease score from 1 to 5 comparing all genotypes in a given test. The score is based on a count of the number of Javanese root-knot nematode galls found on the roots of a plant. A score of 1 indicates there are few galls on the roots. The scores range to a score of 5 which indicates there are many galls.

Lodging: The visual rating of the uprightness of the plants. The score is based on the average of the plants in a plot with a score of 1 to 5, with a score of 1 indicating all plants are erect, and a score of 5 where over about 80% of the plants in a plot are prostrate.

Maturity date: The evaluation of plants considered as mature when about 95% of the pods have reached their mature color.

Peanut Root-knot Nematode: A plant pathogenic nematode (*Meloidogyne arenaria*) that can result in the presence of galls on roots. Resistance or sensitivity to peanut root-knot nematodes is based on a disease score from 1 to 5 comparing all genotypes in a given test. The score is based on a count of the number of peanut root-knot nematode galls found on the roots of a plant. A score of 1 indicates there are few galls on the roots. The scores range to a score of 5 which indicates there are many galls.

Plant: Includes reference to an immature or mature whole plant, including a plant from which seed, roots or leaves have been removed. Seed or embryo that will produce the plant is also considered to be the plant.

Plant height. Plant height is taken from the top of the soil to the tip of the plant, and is typically measured in centimeters or inches.

Plant parts. Includes protoplasts, leaves, stems, roots, root tips, anthers, pistils, seed, embryo, pollen, ovules, cotyledon, hypocotyl, flower, shoot, tissue, petiole, cells, calli, pods, meristematic cells and the like. Includes plant cells of a tissue culture from which soybean plants can be regenerated.

Progeny. Offspring; descendants.

Regeneration. The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Relative maturity: Refers to the maturity grouping designated by the soybean industry over a given growing area. This figure is generally divided into tenths of a relative maturity group. Within narrow comparisons, the difference of a tenth of a relative maturity group equates very roughly to a day difference in maturity at harvest.

Seed. The part of a flowering plant that typically contains the embryo with its protective coat and stored food and that can develop into a new plant under the proper conditions; fertilized and mature ovule.

Seed quality: The visual rating of the completeness of the seed. The score is based on the completeness of the seed coat and overall soundness of the seed. Scores range from 1 to 5, with a score of 1 indicating good quality seed and a score of 5 indicating the seeds are of poor quality.

Seed yield: The yield in bushels/acre (bu/a) and is the actual yield of the grain at harvest.

Self-pollination: The transfer of pollen from the anther to the stigma of the same plant.

Single locus converted (conversion) plant: Plants developed by backcrossing and/or by genetic transformation, wherein essentially all of the desired morphological and physiological characteristics of a soybean variety are recovered in addition to the characteristics of the single locus transferred into the variety via the backcrossing technique.

Southern Root-knot Nematode: A plant-pathogenic nematode (*Meloidogyne incognita*) that attacks the roots of its host plant. Resistance or sensitivity to southern root-knot nematodes is based on a disease score from 1 to 5 comparing all genotypes in a given test. The score is based on a count of the number of southern root-knot nematode galls found on the roots of a plant. A score of 1 indicates there are few galls on the roots to a score of 5 which indicates there are many galls.

Soybean cyst nematode (SCN): A plant-parasitic nematode (*Heterodera glycines*) of the soybean (*Glycine max*). SCN infects the roots of soybean, and the female nematode eventually becomes a cyst. Infection causes various symptoms that can include chlorosis of the leaves and stems, root necrosis, loss in seed yield and suppression of root and shoot growth. SCN field populations vary in their abilities to successfully develop and reproduce on a set of four differential soybean lines that differ genetically in their resistance to SCN. These different populations are referred to as SCN races and are given number designations. There are currently 16 possible reaction combinations and, thus, 16 potential SCN races. At least 12 different races have been reported in the United States, with race 3 the most common in Georgia. Resistance or sensitivity to SCN is based on the presence (sensitive) or absence (resistance) of cysts of SCN.

Tissue culture: A composition that includes isolated cells of the same or a different type or a collection of such cells organized into parts of a plant.

Transformation. The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene. A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a soybean plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

New Soybean Resistant to Race 3 of Soybean Cyst Nematode, Southern, Peanut, and Javanese Root-Knot Nematode The present disclosure relates to a new soybean variety, 'G12PR-63R2'. This new variety is an early Maturing Group (MG) VII (Relative Maturity about 7.3), glyphosate tolerant line, and is resistant to many pests that affect soybeans, including Southern root-knot nematode, Peanut root-knot nematode, Javanese root-knot nematode, and race 3 of the soybean cyst nematode. In some examples, 'G12PR-63R2' also has improved seed yield when compared to one or more existing early MG VII Roundup® Ready cultivars (such as compared to T07M50'). Thus, the new variety is adapted to areas of the United States (such as the southern and southeastern United States) that commonly grow MG VII soybean cultivars and to areas that are known to have or expected to have damaging levels of the Southern root-knot nematode, Peanut root-knot nematode, Javanese root-knot nematode, and/or race 3 of soybean cyst nematode (such as 1, 2, 3 or all 4 of these).

Weeds are a major production problem in the southeastern USA. Roundup® herbicide (glyphosate) is a broad-spectrum herbicide that is highly effective against the major annual and perennial grasses and broad leaved weeds. Roundup Ready 2 Yield® (RR2Y®) is a Monsanto second generation glyphosate tolerance technology that has been reported to provide increased yield of soybean. 'G12PR-63R2' was derived from backcrossing a Monsanto RR2Y line to a high yielding breeding line, 'G00-3880'. 'G12PR-63R2' yielded 1.5 bu/a over the Roundup Ready cultivar 'P97M50', but yielded 2.2 and 4.0 bu/a less than RR2Y commercial cultivars, 'AG7733' and 'AG7934', respectively (Table 5). It matured 1 to 5 days earlier than these cultivars (Table 2). It had similar protein (34%) and oil (18.8%) contents as its recurrent parent and check cultivars (Table 7). In addition, this line possesses resistance to the Southern, Peanut and Javanese root-knot nematodes and race 3 of soybean cyst nematode (Table 6).

'G12PR-63R2' is an MG VII line with the Monsanto second generation glyphosate tolerance technology and with resistance to Southern, Peanut, and Javanese root-knot nematode, and race 3 of the soybean cyst nematode (Table 6). 'G00-3880', a recurrent parent of 'G12PR-63R2', has been tested over 30 locations across southeastern USA and has demonstrated high yield performance and adaptation (Table 8). 'G12PR-63R2' exceeded the yield of Roundup ready cultivar T07M50' by 2.7% (1.5 bu/a) in 10 environments and has similar yield as RR2Y cultivars, 'AG7733' and 'AG7934' across 8 to 10 environments (Table 5). 'G12PR-63R2' has resistance to three species of root-knot nematode and race 3 of SCN which is the predominant race in Georgia and surrounding states. Existing RR2Y varieties do not possess these all of these resistances. 'G12PR-63R2' provides a high yielding RR2Y soybean cultivar with superior nematode resistance to the growers in southeastern USA.

Thus provided herein is a seed of soybean variety 'G12PR-63R2', wherein representative sample seed of the variety will be deposited under (ATCC Accession No. PTA-122508). Also provided are bulk soybean seed containing such seeds. The disclosure provides soybean plants having or consisting of the morphological and physiological characteristics of 'G12PR-63R2'. The disclosure also provides soybean plants having one or more of (such as at least two, at least three, at least four, at least five, at least 6, at least 7, at least 8, at least 9, or at least 10 of) the morphological and physiological characteristics of 'G12PR-63R2' (such as those listed in Tables 1-7). In one example, such plants have or include the characteristics noted in Tables 1-7, for example resistance to Southern root-knot nematode, resistance to Peanut root-knot nematode, resistance to Javanese root-knot nematode, resistance to race 3 of the soybean cyst nematode, glyphosate tolerance, early maturity (such as MG VII), and in some examples also improved seed yield. Also provided are seeds of such plants, progeny of such plants, parts of such plants (such as pollen, ovules and cells). In one example, the disclosure provides soybean plants having the genotype of 'G12PR-63R2'. For example, the disclosure provides plants produced by growing the seed of the new soybean variety 'G12PR-63R2'.

The disclosed 'G12PR-63R2' plants, and in some examples progeny thereof, have increased seed yield as compared to at least one other early Maturity Group VII (MG VII) or mid MG VII soybean, such as 'P07M50' (a mid MG VII soybean). For example, the disclosed 'G12PR-63R2' plants, and in some examples progeny thereof, have a seed yield of at least 50 bu/a (such as at least 51 bu/a, at least 52 bu/a, at least 55 bu/a, or at least 60 bu/a). In some examples, the disclosed 'G12PR-63R2' plants, and in some examples progeny thereof, have a seed yield that is at least 1%, at least 2%, at least 2.5%, or at least 2.7% greater than another early MG VII soybean or a mid MG VII soybean, such as 'P07M50' (a mid MG VII soybean).

In some examples, the disclosed 'G12PR-63R2' plants, and in some examples progeny thereof, have a disease rating for resistance to Southern root-knot nematode of no more than 1.9, no more than 1.8, or no more than 1.7, no more than 1.6, or no more than 1.5 (such as 1 to 1.9, 1 to 1.8, 1 to 1.5, or 1.2 to 1.7), have a disease rating for resistance to Peanut root-knot nematode of no more than 2.5, no more than 2.3, or no more than 2 (such as 1.5 to 2.5, 1 to 2.5, 1 to 2, or 1.8 to 2.2), have a disease rating for resistance to Javanese root-knot nematode of no more than 2.5, no more than 2.3, or no more than 2 (such as 1.5 to 2.5, 1 to 2.5, 1 to 2, or 1.8 to 2.2), are resistant to race 3 of soybean cyst nematode (for example, on average show <10% of females or cysts per plant), or combinations thereof.

The disclosed 'G12PR-63R2' plants and seeds can be used to produce other soybean plants and seeds, for example as part of a breeding program. Choice of breeding or selection methods using to generate new soybean plants and seeds can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location can be effective, whereas for traits with low heritability, selection can be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding can be used to transfer one or a few favorable genes for a highly heritable trait into a desirable variety. This approach has been used extensively for breeding disease-resistant varieties (e.g., see Bowers et al., 1992. *Crop Sci.* 32(1):67-72; Nickell and Bernard, 1992. *Crop Sci.* 32(3):835). Various recurrent selection techniques can be used to improve quantitatively inherited traits controlled by numerous genes.

Promising advanced breeding lines can be thoroughly tested and compared to appropriate standards in environments representative of the commercial target area(s) for generally three or more years. The best or most preferred lines are candidates for new commercial varieties. Those still deficient in a few traits may be used as parents to produce new populations for further selection.

A difficult task is the identification of individuals that are genetically superior, because for most traits the true genotypic value can be masked by other confounding plant traits or environmental factors. One method of identifying a superior plant is to observe its performance relative to other experimental plants and to one or more widely grown standard varieties. Single observations can be generally inconclusive, while replicated observations provide a better estimate of genetic worth.

Plant breeding can result in new, unique and superior soybean varieties and hybrids from 'G12PR-63R2'. Two or more parental lines can be selected (such as 'G12PR-63R2' as one of the lines), followed by repeated selfing and selection, producing many new genetic combinations. Each year, the germplasm to advance to the next generation is selected. This germplasm is grown under unique and different geographical, climatic and soil conditions, and further selections are then made, during and at the end of the growing season. The varieties developed can be unpredictable, because the selection occurs in unique environments, with no control at the DNA level (using conventional breeding procedures), and with millions of different possible genetic combinations being generated.

The development of new soybean varieties from 'G12PR-63R2' involves the development and selection of soybean varieties, the crossing of these varieties and selection of progeny from the superior hybrid crosses. A hybrid seed is produced by manual crosses between selected male-fertile parents or by using male sterility systems. Hybrids can be identified by using certain single locus traits such as pod color, flower color, seed color, pubescence color or herbicide tolerance which indicate that the seed is truly a hybrid. Additional data on parental lines as well as the phenotype of the hybrid can influence a decision whether to continue with the specific hybrid cross.

Pedigree breeding and recurrent selection breeding methods can be used to develop varieties from breeding populations. Breeding programs combine desirable traits from two or more varieties or various broad-based sources into breeding pools from which varieties are developed by selfing and selection of desired phenotypes. Pedigree breeding is commonly used for the improvement of self-pollinating crops. Two parents (e.g., wherein one of the parents is 'G12PR-63R2') which possess favorable, complementary traits are crossed to produce an $F_1$. An F2 population is produced by selfing one or several $F_1$'s. Selection of the best or most preferred individuals can begin in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (i.e., $F_6$ and $F_7$), the best lines or mixtures of phenotypically similar lines can be tested for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety which is the recurrent parent (e.g., 'G12PR-63R2'). The source of the trait to be transferred is called the donor or nonrecurrent parent. The resulting plant is typically expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population are represented by a progeny when generation advance is completed.

In a multiple-seed procedure, one or more pods from each plant in a population are commonly harvested and threshed together to form a bulk. Part of the bulk is used to plant the next generation and part is put in reserve. The procedure has been referred to as modified single-seed descent or the pod-bulk technique. The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Sufficient numbers of seeds are harvested to make up for those plants that did not germinate or produce seed.

Descriptions of other breeding methods that are commonly used for different traits and crops can be found in one of several reference books (e.g., Allard. 1960. Principles of plant breeding. Davis, Calif.: John Wiley & Sons, NY, University of California, pp. 50-98; Simmonds. 1979. Principles of crop improvement. New York: Longman, Inc., pp. 369-399; Sneep and Hendriksen. 1979. "Plant breeding perspectives." Wageningen (ed.), Center for Agricultural Publishing and Documentation; Fehr. 1987. "Principles of variety development." Theory and Technique (Vol. 1) and Crop Species Soybean (Vol. 2). New York: Macmillian Publishing Company, Iowa State University, pp. 360-376).

Breeding Soybean Variety 'G12PR-63R2'

Methods for crossing the new soybean variety 'G12PR-63R2' with itself or a second plant are provided, as are the seeds and plants produced by such methods. Such methods can be used for propagation of the new soybean variety 'G12PR-63R2', or can be used to produce hybrid soybean seeds and the plants grown therefrom. Hybrid soybean plants can be used, for example, in the commercial production of soy products or in breeding programs for the production of novel soybean varieties. A hybrid plant can also be used as a recurrent parent at any given stage in a backcrossing protocol during the production of a single locus conversion (for example introduction of one or more desirable traits) of the new soybean variety 'G12PR-63R2'.

Methods of producing soybean plants and/or seed are provided. Such a method can include crossing the new soybean variety 'G12PR-63R2' with itself or a second soybean plant and harvesting a resulting soybean seed, such as an $F_1$ hybrid seed. The resulting plant can be grown, resulting in a soybean plant or part thereof.

In one example methods of producing an inbred soybean plant derived from soybean variety 'G12PR-63R2' are provided. In one example such methods include (a) preparing a progeny plant derived from soybean variety 'G12PR-63R2' by crossing a plant of the soybean variety 'G12PR-63R2' with a soybean plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred soybean plant derived from the soybean variety 'G12PR-63R2'.

The second plant crossed with the new soybean variety 'G12PR-63R2' for the purpose of developing novel soybean varieties, is typically a plant which either themselves exhibit one or more desirable characteristics or which exhibit one or more desired characteristic(s) when in hybrid combination. In one example, the second soybean plant is transgenic. Exemplary desired characteristics include, but are not limited to: increased seed yield, lodging resistance, emergence, increased seedling vigor, modified maturity date, desired plant height, high oil content, high protein content, herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance; modified phosphorus characteristics; modified antioxidant characteristics; modified essential seed amino acid characteristics; modified fatty acid metabolism, modified carbohydrate metabolism, and modified soybean fiber characteristics.

When the new soybean variety 'G12PR-63R2' is crossed with another different variety, first generation ($F_1$) soybean progeny are produced. The hybrid progeny are produced regardless of characteristics of the two varieties produced. As such, an $F_1$ hybrid soybean plant can be produced by crossing 'G12PR-63R2' with any second soybean plant. The second soybean plant can be genetically homogeneous (e.g., inbred) or can itself be a hybrid. Therefore the disclosure provides any $F_1$ hybrid soybean plant produced by crossing the new soybean variety 'G12PR-63R2' with a second soybean plant (such as a transgenic plant having one or more genes that confer to the plant one or more desired characteristics).

Soybean plants (*Glycine max*) can be crossed by either natural or mechanical techniques (see, e.g., Fehr. 1980. "Soybean." In: Hybridization of Crop Plants. Fehr and Hadley (eds). Madison, Wis.: *Am. Soc. Agron., Crop Sci. Soc. Am.*, pp. 590-599). Natural pollination occurs in soybeans either by self pollination or natural cross pollination, which typically is aided by pollinating organisms. In either natural or artificial crosses, flowering and flowering time can be a consideration. Soybean is a short-day plant, but there is considerable genetic variation for sensitivity to photoperiod. The critical day length for flowering can range from about 13 hours for genotypes adapted to tropical latitudes to about 24 hours for photoperiod-insensitive genotypes grown at higher latitudes. Soybeans can be insensitive to day length for about 9 days after emergence. Photoperiods shorter than the critical day length can be needed for approximately 7 days to approximately 26 days to complete flower induction.

Sensitivity to day length can be a consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting (Fehr. 1980. "Soybean." In: Hybridization of Crop Plants. Fehr and Hadley (eds). Madison, Wis.: *Am. Soc. Agron., Crop Sci. Soc. Am., pp.* 590-599). Soybeans can be grown in winter nurseries located at sea level in tropical latitudes where day lengths are shorter than their critical photoperiod. The short day lengths and warm temperatures encourage early flowering and seed maturation, and genotypes can produce a seed crop in about 90 days or fewer after planting. Early flowering can be useful for generation advance when only a few self-pollinated seeds per plant are desired, but usually not for artificial hybridization because the flowers self-pollinate before they are large enough to manipulate for hybridization. Artificial lighting can be used to extend the natural day length to about 14.5 hours to obtain flowers suitable for hybridization and to increase yields of self-pollinated seed. The effect of a short photoperiod on flowering and seed yield can be partly offset by altitude. At tropical latitudes, varieties adapted to the northern U.S. perform more like those adapted to the southern U.S. at high altitudes than they do at sea level. The light level for delay of flowering can be dependent on the quality of light emitted from the source and the genotype being grown. For example, blue light with a wavelength of about 480 nm typically needs more than about 30 times the energy to inhibit flowering as red light with a wavelength of about 640 nm (Parker et al. 1946. *Bot. Gaz.* 108:1-26).

Temperature can also affect the flowering and development of soybean. It can influence the time of flowering and suitability of flowers for hybridization. Temperatures below about 21° C. or above about 32° C. can reduce floral initiation or seed set (Hammer. 1969. "*Glycine max* (L.) Merrill." In: The Induction of Flowering: Some Case Histories. Evans (ed). Ithaca, N.Y.: Cornell University Press, pp. 62-89; van Schaik and Probst. 1978. *Agron. J.* 50:192-197). Artificial hybridization is typically successful between about 26° C. and about 32° C. because cooler temperatures can reduce pollen shed and result in flowers that self-pollinate before they are large enough to manipulate. Warmer temperatures can be associated with increased flower abortion caused by moisture stress; however, successful crosses can be achieved up to about 35° C. if soil moisture is adequate.

Soybeans are classified as indeterminate, semi-determinate, and determinate based on the abruptness of stem termination after flowering begins. When grown at their latitude of adaptation, indeterminate genotypes flower when about one-half of the nodes on the main stem have developed. They have short racemes with few flowers, and their terminal node has only a few flowers. Semi-determinate genotypes also flower when about one-half of the nodes on the main stem have developed, but node development and flowering on the main stem stops more abruptly than on indeterminates. Their racemes are short and have few flowers, except for the terminal one, which may have several times more flowers than those lower on the plant. Determinate varieties begin flowering when all or most of the nodes on the main stem have developed. They usually have elongated racemes that may be several centimeters in length and may have a large number of flowers.

Soybean flowers typically are self-pollinated on the day the corolla opens. The amount of natural crossing, which is typically associated with insect vectors such as honeybees, is approximately 1% for adjacent plants within a row and approximately 0.5% between plants in adjacent rows. The structure of soybean flowers is similar to that of other legume species and consists of a calyx with approximately five sepals, a corolla with approximately five petals, approximately ten stamens, and a pistil. The stigma is receptive to pollen about 1 day before anthesis and remains receptive for approximately 2 days after anthesis, if the flower petals are not removed. The anthers dehisce on the day of anthesis, pollen grains fall on the stigma, and within approximately 10 hours, the pollen tubes reach the ovary and fertilization is completed.

Self-pollination can occur naturally in soybean with no manipulation of the flowers. In some examples, the crossing of two soybean plants is accomplished using artificial hybridization. In artificial hybridization, the flower used as a female in a cross is manually cross pollinated prior to maturation of pollen from the flower, thereby preventing self fertilization, or alternatively, the male parts of the flower are emasculated using known methods. Exemplary methods for emasculating the male parts of a soybean flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed, for example with forceps. Immature buds, such as those hidden under the stipules at the leaf axil, are removed. The calyx is removed, for example by grasping a sepal with the forceps, pulling it down and around the flower, and repeating the procedure until the five sepals are removed. The exposed corolla is removed, for example by grasping it just above the calyx scar, then lifting and wiggling the forceps simultaneously. The ring of anthers is visible after the corolla is removed, unless the anthers were removed with the petals. Cross-pollination can then be performed using, for example, petri dishes or envelopes in which male flowers have been collected. Desiccators containing calcium chloride crystals are used in some environments to dry male flowers to obtain adequate pollen shed.

Emasculation is not necessary to prevent self-pollination (Walker et al. 1979. *Crop Sci.* 19:285-286). When emasculation is not used, the anthers near the stigma can be removed to make the stigma visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Pollen is available from a flower with a recently opened corolla, but the degree of corolla opening associated with pollen shed can vary during the day. In many environments, collection and use of male flowers immediately without storage can be conducted. In the southern U.S. and other humid climates, pollen shed occurs in the morning when female flowers are more immature and difficult to manipulate than in the afternoon, and the flowers can be damp from heavy dew. In those circumstances, male flowers are collected into envelopes or petri dishes in the morning, and the open container is typically placed in a desiccator for about 4 hours at a temperature of about 25° C. The desiccator can be taken to the field in the afternoon and kept in the shade to prevent excessive temperatures from developing within it. Pollen viability can be maintained in flowers for up to about 2 days when stored at about 5° C. In a desiccator at about 3° C., flowers can be stored successfully for several weeks; however, varieties can differ in the percentage of pollen that germinates after long-term storage.

Either with or without emasculation of the female flower, hand pollination can be carried out by removing the stamens and pistil from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and high percentages of successful crosses are typically obtained when pollen is clearly visible on the stigma. Pollen shed can be checked by tapping the anthers before brushing the stigma. Several male flowers can be used to obtain suitable pollen shed when conditions are unfavorable, or the same male can be used to pollinate several flowers with good pollen shed.

When male flowers are not collected and dried in a desiccator, the parents of a cross can be planted adjacent to each other. Plants are typically grown in rows about 65 cm to about 100 cm apart. Yield of self-pollinated seed from an individual plant can range from a few seeds to more than about 1,000 as a function of plant density. A density of about 30 plants/m of row can be used when about 30 or fewer seeds per plant is adequate, about 10 plants/m can be used to obtain about 100 seeds/plant, and about 3 plants/m usually results in a high seed production per plant. Densities of about 12 plants/m or less are commonly used for artificial hybridization.

Multiple planting dates about 7 days to about 14 days apart can typically be used to match parents of different flowering dates. When differences in flowering dates are extreme between parents, flowering of the later parent can be hastened by creating an artificially short day. Alternatively, flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 hours for about 15 days beginning when there are three nodes with trifoliate leaves on the main stem. Plants induced to flower early tend to have flowers that self-pollinate when they are small and can be difficult to prepare for hybridization.

Grafting can be used to hasten the flowering of late flowering genotypes. A scion from a late genotype grafted on a stock that has begun to flower can begin to bloom up to about 42 days earlier than normal. First flowers on the scion can appear from about 21 days to about 50 days after the graft.

Observing pod development approximately 7 days after pollination is generally sufficient to identify a successful cross. Abortion of pods and seeds can occur several weeks after pollination, but the percentage of abortion is typically low if plant stress is minimized. Pods that develop from artificial hybridization can be distinguished from self-pollinated pods by the presence of the calyx scar, caused by removal of the sepals. The sepals typically begin to fall off as the pods mature; therefore, harvest can be completed at or immediately before the time the pods reach their mature color. Harvesting pods early also avoids any loss by shattering.

Once harvested, pods are typically air-dried at not more than about 38° C. until the seeds contain approximately 13% moisture or less. The seeds are then removed. Seed can be stored at about 25° C. for up to a year if relative humidity is approximately 50% or less. In humid climates, germination percentage declines rapidly unless the seed is dried to about 7% moisture and stored in an air-tight container at room temperature. Long-term storage in any climate can be accomplished by drying seed to about 7% moisture and storing it at about 10° C. or less in a room maintained at about 50% relative humidity or in an air-tight container.

Soybean Plants Having One or More Desired Heritable Traits

The disclosure provides plants of the new soybean variety 'G12PR-63R2' modified to include one or more desired heritable traits. In some examples, such plants can be developed using backcrossing or genetic engineering (for example by introducing one or more transgenes into the 'G12PR-63R2' variety, wherein the transgenes encode one or more desired traits), wherein essentially all of the desired morphological and physiological characteristics of the 'G12PR-63R2' variety are recovered (such as 2, 3, 4, 5 or all 6 of resistance to southern root-knot nematode, resistance to Javanese root-knot nematode, resistance to race 3 of soybean cyst nematode, resistance to Peanut root-knot nematode, tolerance to glyphosate, and early maturity (e.g., MG VII)) in addition to a genetic locus transferred into the plant via the backcrossing technique. Plants developed using such methods can be referred to as a single locus converted plant.

In one example, the method of introducing one or more desired traits into soybean variety 'G12PR-63R2' includes (a) crossing a plant of variety 'G12PR-63R2' with a second plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of variety 'G12PR-63R2' to produce backcross progeny plants; (d) selecting backcross progeny plants that have the one or more desired traits and physiological and morphological characteristics of soybean variety 'G12PR-63R2' to produce selected backcross progeny plants; and (e) repeating steps (c) and (d) one or more times in succession to produce selected second or higher backcross progeny plants that have the one or more desired traits and the physiological and morphological characteristics of soybean variety 'G12PR-63R2' when grown in the same environmental conditions.

Backcrossing methods can be used to improve or introduce a characteristic into the new soybean variety 'G12PR-63R2' (for example using the methods provided in U.S. Pat. No. 6,140,556). The parental soybean plant which contributes the locus for the desired characteristic is termed the "nonrecurrent" or "donor" parent. This terminology refers to the fact that the nonrecurrent parent is used one time in the backcross protocol and therefore does not recur. The parental soybean plant to which the locus or loci from the nonrecurrent parent are transferred is known as the recurrent parent as it is used for several rounds in the backcrossing protocol (Poehlman and Sleper. 1995. "Breeding Field Crops" Ames, Iowa: Iowa State University Press; Fehr. 1987. "Principles of variety development." In Theory and Technique (Vol. 1) and Crop Species Soybean (Vol. 2). New York: Macmillan Publishing Company, pp. 360-376; Sprague and Dudley, eds. 1988. Corn and Improvement, 3rd edition). In a typical backcross protocol, the original variety of interest (recurrent parent, e.g., 'G12PR-63R2') is crossed to a second variety (nonrecurrent parent) that carries the single locus of interest (such as a desirable trait) to be transferred. The resulting progeny from this cross are then crossed again to the recurrent parent and the process is repeated until a soybean plant is obtained wherein essentially all of the desired morphological and physiological characteristics of the recurrent parent (e.g., 'G12PR-63R2') are recovered (such as resistance to Southern root-knot nematode, Javanese root-knot nematode, race 3 of soybean cyst nematode, and Peanut root-knot nematode, as well as tolerance to glyphosate, and early maturity (e.g., MG VII)) in the converted plant, in addition to the single transferred locus from the nonrecurrent parent.

The goal of a backcross protocol is to alter or substitute a single trait or characteristic in the original variety, such as 'G12PR-63R2'. To accomplish this, a single locus of the recurrent variety is modified or substituted with the desired locus from the nonrecurrent parent, while retaining essentially all of the rest of the desired genetic traits, and therefore the desired physiological and morphological constitution of the original variety. The choice of the particular nonrecurrent parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield or resistance to a pest. As in this example, lines with the phenotype of the recurrent parent can be composited without the usual replicated tests for traits such as yield, protein or oil percentage in the individual lines.

Soybean varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease, insect resistance, restoration of male fertility, enhanced nutritional quality, modified phosphorus characteristics, modified antioxidant characteristics, modified essential seed amino acid characteristics, modified fatty acid metabolism, modified carbohydrate metabolism, and modified soybean fiber characteristics, yield stability, and yield enhancement. These comprise genes generally inherited through the nucleus. Thus plants of soybean variety 'G12PR-63R2' that include a single locus conversion (such as one that confers a desired trait) are provided herein.

Direct selection can be applied where the single locus acts as a dominant trait. An example of a dominant trait is the herbicide resistance trait (such as glyphosate tolerance). For the selection process, the progeny of the initial cross are sprayed with an herbicide (such as Roundup®) prior to the backcrossing. The spraying eliminates any plants which do not have the desired herbicide tolerance characteristic; only those plants which have the herbicide resistance gene are used in the subsequent backcross. This process is then repeated for all additional backcross generations.

Selection of soybean plants for breeding may not be dependent on the phenotype of a plant and instead can be based on genetic investigations. For example, a suitable genetic marker can be used which is closely genetically linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to the breeding of soybeans are well known in the art. Such methods can be useful in the case of recessive traits and variable phenotypes, or where conventional assays are more expensive, time consuming or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, incorporated herein by reference), and Single Nucleotide Polymorphisms (SNPs).

Qualitative characters can be useful as phenotype-based genetic markers in soybeans; however, some or many may not differ among varieties commonly used as parents. Widely used genetic markers include flower color (purple dominant to white), pubescence color (brown dominant to gray), and pod color (brown dominant to tan). Differences in maturity, height, hilum color, and pest resistance between parents can also be used to verify hybrid plants.

Useful or desirable traits can be introduced by backcrossing, as well as directly into a plant by genetic transformation methods. Genetic transformation can therefore be used to insert a selected transgene into the 'G12PR-63R2' variety or can, alternatively, be used for the preparation of transgenes which can be introduced by backcrossing. Thus, the disclosure provides methods of producing a plant of soybean variety 'G12PR-63R2' that includes one or more added desired traits, for example that include introducing a transgene(s) conferring the one or more desired traits into a plant of soybean variety 'G12PR-63R2' (for example by transformation with a transgene that confers upon the soybean plant the desired trait), thereby producing a plant of soybean variety 'G12PR-63R2' that includes the one or more added desired traits.

Methods for the transformation of many economically important plants, including soybeans, are well known. Methods for introducing a desired nucleic acid molecule (e.g., transgene), such as DNA, RNA, or inhibitory RNAs, are well known in the art, and the disclosure is not limited to particular methods. Exemplary techniques which can be employed for the genetic transformation of soybeans include, but are not limited to, electroporation, microprojectile bombardment, *Agrobacterium*-mediated transformation and direct DNA uptake by protoplasts.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner.

Protoplasts can also be employed for electroporation transformation of plants (Bates. 1994. *Mol. Biotechnol.* 2(2):135-145; Lazzeri. 1995. *Methods Mol. Biol.* 49:95-106). For example, the generation of transgenic soybean plants by electroporation of cotyledon-derived protoplasts has been described by Dhir and Widholm (WO 1992/017598).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target soybean cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large. Microprojectile bombardment methods can be used to transform soybeans, as described, for example, in U.S. Pat. No. 5,322,783.

*Agrobacterium*-mediated transfer is a well-known method in the art for introducing gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is well known (e.g., Fraley et al. 1985. *Bio. Tech.* 3(7):629-635; U.S. Pat. No. 5,563,055), and its use for soybean transformation has been described (Chee and Slightom. 1995. *Methods Mol. Biol.* 44:101-119; U.S. Pat. No. 5,569,834). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319(6056): 791-739; Uchimiya et al. 1986. *Mol. Gen. Genet.* 204(2):207-207; Marcotte et al. 1988. *Nature* 335(6189):454-457). The ability to regenerate soybean plants from protoplasts makes these techniques applicable to soybean (Dhir et al. 1991. *Plant Cell Rep.* 10(2):97-101).

In one example, such methods can also be used to introduce transgenes for the production of proteins in transgenic soybeans. The resulting produced protein can be harvested from the transgenic soybean. The transgene can be harvested from the transgenic plants that are originated or are descended from the new soybean variety 'G12PR-63R2', a seed of 'G12PR-63R2' or a hybrid progeny of 'G12PR-63R2'.

Numerous different genes are known and can be introduced into a soybean plant 'G12PR-63R2' or progeny thereof. Non-limiting examples of particular genes and corresponding phenotypes that can be chosen for introduction into a soybean plant are provided herein.

Herbicide Resistance

Numerous herbicide resistance genes are known and can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to an herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricinacetyl transferase (bar) genes) can be used (e.g., see U.S. Pat. No. 4,940,835). Examples of specific EPSPS transformation events conferring glyphosate resistance are described, for example, in U.S. Pat. No. 6,040,497.

DNA molecules encoding a mutant aroA gene are known (e.g., ATCC accession number 39256 and U.S. Pat. No. 4,769, 061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of transgenic plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Genes conferring resistance to an herbicide that inhibits photosynthesis are also known, such as, a triazine (psbA and gs+genes) and a benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseuodmonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is well known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161 (1):85-90) and Evans et al. (1971. *Biochem J* 122(4):543-551).

Disease Resistance

Plant defenses are often activated by specific interaction between the product of a disease resistance gene (R) in the plant and the product of a corresponding avirulence (Avr) gene in the pathogen. A plant, such as 'G12PR-63R2' or progeny thereof, can be transformed with cloned resistance gene to engineer plants that are resistant to specific pathogen strains. See, for example Jones et al. (1994. *Science* 266:789) (tomato Cf-9 gene for resistance to *Cladosporium flavum*); Martin et al. (1993. *Science* 262(5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclose transgenic plants expressing a barley ribosome-inactivating gene have an increased resistance to fungal disease.

Insect Resistance

One example of an insect resistance gene includes a *Bacillus thuringiensis* (Bt) protein, a derivative thereof or a synthetic polypeptide modeled thereon (e.g., see Geiser et al., 1986. *Gene* 48:109, discloses a Bt Δendotoxin gene). Moreover, DNA molecules encoding A-endotoxin genes can be purchased from the ATCC (Manassas, Va.), for example under ATCC Accession Nos. 40098, 67136, 31995 and 31998. Another example is a lectin. See, for example, Van Damme et al. (1994. *Plant Mol Biol* 24(5):825-830), which discloses several *Clivia miniata* mannose-binding lectin genes. A vitamin-binding protein can also be used, such as avidin. See WIPO Publication No. WO 1994/000992, which teaches the use of avidin and avidin homologues as larvicides against insect pests.

In one example the insect resistance gene is an enzyme inhibitor, for example, a protease, proteinase inhibitor, or an α-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. *Nature* 344:458-461; discloses juvenile hormone esterase, an inactivator of juvenile hormone).

Still other examples include an insect-specific antibody or an immunotoxin derived therefrom and a developmental-arrestive protein. See Taylor et al. (1994. Seventh Intl. Symposium on Molecular Plant-Microbe Interactions (Edinburgh Scotland), Abstract #497), who described enzymatic inactivation in transgenic tobacco via production of single-chain antibody fragments.

Male Sterility

Genetic male sterility is available in soybeans and can increase the efficiency with which hybrids are made, in that it can eliminate the need to physically emasculate the soybean plant used as a female in a given cross (Brim and Stuber. 1973. *Crop Sci.* 13:528-530). Herbicide-inducible male sterility systems are known (e.g., U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the soybean plant is utilized. However, in many cases, the seeds are considered to be a valuable portion of the crop, thus, it is desirable to restore the fertility of the hybrids in these crops. Therefore, the disclosure provides plants of the new soybean variety 'G12PR-63R2' comprising a genetic locus capable of restoring male fertility in an otherwise male-sterile plant. Examples of male-sterility genes and corresponding restorers which can be employed are known (see, e.g., U.S. Pat. No. 5,530,191 and U.S. Pat. No. 5,684,242).

Modified Fatty Acid, Phytate and Carbohydrate Metabolism

Genes conferring modified fatty acid metabolism can be introduced into 'G12PR-63R2' and its progeny, such as antisense stearoyl acyl carrier protein (ACP) desaturase genes (EC 1.14.99.6) (e.g., Knutzon et al. 1992. *PNAS* 89:2624-2628). Fatty acid desaturases can be introduced into 'G12PR-63R2' and its progeny, such as *Saccharomyces cerevisiae* OLE1 gene encoding 49-fatty acid desaturase, an enzyme which forms the monounsaturated palmitoleic (16:1) and oleic (18:1) fatty acids from palmitoyl (16:0) or stearoyl (18:0) CoA (McDonough et al., 1992. *J Biol Chem* 267(9): 5931-5936); a gene encoding a stearoyl-acyl carrier protein Δ-9 desaturase from castor (Fox et al. 1993. *PNAS* 90(6): 2486-2490); Δ 6- and Δ12-desaturases from the cyanobacteria *Synechocystis* responsible for the conversion of linoleic acid (18:2) to gamma-linolenic acid (18:3 gamma) (Reddy et al., 1993. *Plant Mol Biol* 22(2):293-300); a gene from *Arabidopsis thaliana* that encodes an omega-3 desaturase (Arondel et al. 1992. *Science* 258:1353-5); plant Δ 9-desaturases (WIPO Publication No. WO 1991/013972) and soybean and *Brassica* Δ15 desaturases (European Patent Application Publ. No. EP 0616644).

Phytate metabolism can also be modified by introduction of a phytase-encoding gene to enhance breakdown of phytate, adding more free phosphate to the transformed plant. For example, see Van Hartingsveldt et al. (1993. *Gene* 127:87-94), for an *Aspergillus niger* phytase gene. In soybean, this, for example, could be accomplished by cloning and then reintroducing DNA associated with the single allele which is responsible for soybean mutants characterized by low levels of phytic acid. See Raboy et al. (2000, *Plant Physiol.* 124(1): 355-68).

A number of genes are known that can be used to alter carbohydrate metabolism. For example, plants can be transformed with a gene coding for an enzyme that alters the branching pattern of starch. See Shiroza et al. (1988. *J Bacteriol* 170(2):810-816) (*Streptococcus* fructosyltransferase gene), Steinmetz et al. (1985. Mol Gen Genet. 200:220-228) (*Bacillus subtilis* levansucrase gene), Pen et al. (1992. *BioTechnology* 10:292) (*Bacillus lichenifonnis* α-amylase), Elliot et al. (1993. *Plant Mol. Biol* 21:515) (tomato invertase genes), Sergaard et al. (1993. *J. Biol. Chem.* 268:22480) (site-directed mutagenesis of barley α-amylase gene), and Fisher et al. (1993. *Plant Physiol* 102:1045) (maize endosperm starch branching enzyme II). The Z10 gene encoding a 10 kD zein storage protein from maize can also be used to alter the quantities of 10 kD zein in the cells relative to other components (Kirihara et al., 1988. *Mol Gen Genet.* 211:477-484).

Modifications can also include site-specific recombination; abiotic stress tolerance; modified antioxidant characteristics; modified essential seed amino acid characteristics, or the like, or any combination thereof. Merely by way of example, FRT sites and/or Lox sites can be introduced into a soybean plant. FRT sites can be used in the FLP/FRT system. Lox sites can be used in the Cre/Loxp system. Abiotic stress tolerance can include, but is not limited to, tolerance to stress induced by, for example, flowering, ear and seed development, enhancement of nitrogen utilization efficiency, altered nitrogen responsiveness, drought resistance or tolerance, cold resistance or tolerance, heat resistance or tolerance, low or high soil pH level resistance or tolerance, and salt resistance or tolerance. Such abiotic stress tolerance can increase yield under stress. Modifications can be made to a soybean plant to introduce modified antioxidant characteristics (e.g., content or composition, such as alteration of tocopherol or tocotrienols), modified essential seed amino acid characteristics (e.g., increasing accumulation of essential amino acids in seeds). Exemplary useful genes and traits for transgenic modification of the variety are disclosed in, for example, U.S. Pat. Nos. 7,687,686, 7,649,127 and 7,645,923.

Tissue Cultures and In Vitro Regeneration of Soybean Plants

Tissue cultures of the new soybean variety 'G12PR-63R2' are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, pod, petiole, stein, ovule, cotyledon, hypocotyl, shoot or stem, and the like. In a particular example, the tissue culture includes embryos, protoplasts, meristematic cells, pollen, leaves or anthers of the new soybean variety 'G12PR-63R2'. Also provided are soybean plants regenerated from such tissue cultures, wherein the regenerated soybean plant expresses the physiological and morphological characteristics of the soybean variety 'G12PR-63R2'.

Soybeans are typically regenerated using shoot morphogenesis or somatic embryogenesis (Finer et al. 1996. "Soybean transformation: Technologies and progress." In: Soybean: Genetics, Molecular Biology and Biotechnology. Verma and Shoemaker (eds). Wallinford, Oxon, UK: CAB International, pp. 250-251). Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos, while lines that produce large numbers of embryos during an "induction" step may not give rise to rapidly-growing proliferative cultures. In addition to line-specific responses, proliferative cultures can be observed with both shoot morphogenesis and somatic embryogenesis. Proliferation allows a single, transformed cell to multiply to the point that it can contribute to germ-line tissue.

Shoot morphogenesis is a system whereby shoots are obtained de novo from cotyledonary nodes of soybean seedlings (Wright et al., 1986. *Plant Cell Reports* 5:150-154). The shoot meristems form subepidermally and morphogenic tissue can proliferate on a medium containing benzyl adenine (BA). This system can be used for transformation if the subepidermal, multicellular origin of the shoots is recognized and proliferative cultures are utilized. Tissue that can give rise to new shoots are targeted and proliferated within the meristematic tissue to lessen problems associated with chimerism.

Somatic embryogenesis in soybean is a system in which embryogenic tissue is obtained from the zygotic embryo axis (Christianson et al., 1983. *Science* 222:632-634). The embryogenic cultures are proliferative and the proliferative embryos are of apical or surface origin with a small number of cells contributing to embryo formation. The origin of primary embryos (the first embryos derived from the initial explant) is dependent on the explant tissue and the auxin levels in the induction medium (Hartweck et al., 1988. *In Vitro Cell. Develop. Bio.* 24:821-828). With proliferative embryonic cultures, single cells or small groups of surface cells of the "older" somatic embryos form the "newer" embryos.

Embryogenic cultures can also be used for regeneration, including regeneration of transgenic plants.

EXAMPLE 1

Breeding History of 'G12PR-63R2'

'G12PR-63R2' originated from the DNA marker-assisted backcross of 'G00-3880' (5)×'NC7308A1-COYN'. 'G00-3880' is a high yielding breeding line from the cross of 'G93-9201' and 'Cook' (Boerma et al., *Crop Sci.* 32:497, 1992). 'G93-9201' was developed from the cross' G83-559'×['G80-1515' (2)×'PI 230977'], wherein 'G83-559'=D77-6103×$F_{77}$-6903. D77-6103='Centennial'×J74-47 and J74-47='Forrest' (2)×D68-18×P188788. D68-18='Dyer'×'Bragg'. G93-9201 is a sister line of the released Javanese root-knot resistant germplasm line, G93-9223 (Luzzi et al., *Crop Sci.* 37:1035-1036, 1997). The NC7308A1-COYN line contains the MON 89788 event (Monsanto's Roundup Ready 2 Yield™ trait; RR2Y) which results in the expression of the enzyme 5-enolpyruvylshikimate-3-phosphate synthase from *Agrobacterium* sp. Strain CP4 (CP4 EPSPS) that allows the plant to tolerate application of the broad spectrum herbicide glyphosate (Malven et al., US 2006/0282915). The pedigree of NC7308A1-COYN is not known by the inventors.

The original cross of 'G00-3880'×'NC7308A1-COYN' was made' and the F2 seed were provided to the inventors in the spring of 2008. BC1F1 seed was produced by crossing glyphosate-tolerant F2 plants from the 'G00-3213'× 'NC7308A1-COYN' population with 'G00-3880' in the summer of 2008. In the winter of 2009, the DNA from 66 BC1F1 plants that were tolerant to glyphosate was analyzed with the 1,536 SNP array. The SNPs in this array have been previously selected for their distribution across the soybean genome. A total of 389 of these SNPs were polymorphic between 'G0-3213' and 'NC7308A1-COYN'. The 46 BCIF1 plants varied from 57 to 90% similarity to 'G00-3880' based on these 464 polymorphic SNPs.

The BC1F1 plant with 90% SNP allele similarity to 'G00-3880' was selected (marker-assisted recurrent parent background selection) as pollen sources for the next backcross. Due to the marker-assisted background selection with SNP markers these two plants will hereafter be referred to as $BC2F_1$ plants rather than BC1F1 plants. The $BC3F_1$ seed was produced in an Athens, Ga. greenhouse during the spring of 2009. During the summer of 2009 the BC4F1 seed was produced by obtaining pollen from glyphosate tolerant FC3F1 plants to cross with G00-3880. The BC4F1 plants were grown in an Athens, Ga. greenhouse during the winter of 2010 and sprayed with glyphosate.

During the summer of 2010 the BC4F2 generation was grown at the Plant Sciences Farm near Athens, Ga. Glyphosate was applied and at maturity the tolerant plants were sampled by single seed descent. The BC4F3 and BC4F4 generations were grown in a winter nursery in Puerto Rico during the winter of 2011 both generations were treated with glyphosate. During the summer of 2011 the BC4F5 generation was grown at the Plant Sciences Farm near Athens, Ga. and treated with glyphosate. In the fall of 2011 32 glyphosate-tolerant plants were harvested individually (created BC4F5-derived lines) and sent to a winter nursery in Puerto Rico for a seed increase. This increase was produced in the lighted area of the winter nursery to provide a maximum seed increase.

Thirty lines were returned to Georgia in May of 2012 and planted at Athens and Plains, Ga. in a replicated yield test. An increase of G12PR-63R2 was grown in a winter nursery in Puerto Rico during the winter of 2013 and was treated with glyphosate. In the summer of 2013 G12PR-63R2 was grown at 13 locations. A Breeder seed increase of 'G12PR-63R2' was grown on 18 acres in 2013. As with previous seed increases, glyphosate was applied to the Breeder seed increase. There were no glyphosate intolerant plants found in the Breeder seed increase.

EXAMPLE 2

Description of 'G12PR-63R2'

'G12PR-63R2' is an early Maturity Group (MG) VII (Relative Maturity 7.3), glyphosate-tolerant strain with purple flowers, tawny pubescence, and tan pod walls. It averages the two days earlier in maturity than 'G00-3880' the recurrent parent, one day earlier than 'P97M50', and two to three days earlier than 'AG7733' (Tables 1, 2, and 3). It has yellow seeds with dull seed coats and black hila. Seed of 'G12PR-63R2' average 11 mg/seed smaller than 'G00-3880' and 35 mg/seed smaller than 'AG7733' (Tables 1 and 2).

TABLE 1

Mean performance of 'G12PR-63R2' and test strains in two Georgia trials in 2012.

| Strain | Seed yield (bu/a) | Maturity date | Plant height | Lodging rating[1] | Seed weight (mg/seed) | Seed quality rating[2] |
|---|---|---|---|---|---|---|
| G12PR-63R2 | 62.7a[3] | 10-16 | 30 | 1.0 | 154 | 1.5 |
| G00-3880 | 57.4a | 10-18 | 28 | 1.1 | 163 | 1.9 |
| AG7733 | 58.4a | 10-18 | 30 | 1.0 | 189 | 1.5 |
| AG7231 | 60.8a | 10-18 | 29 | 1.2 | 189 | 1.6 |
| AG7532 | 59.6a | 10-20 | 29 | 1.2 | 177 | 1.6 |
| AG7333 | 56.1a | 10-16 | 28 | 1.2 | 181 | 1.9 |

[1]Rating: 1 (all plants erect) to 5 (over 80% of plants prostrate).
[2]Rating: 1 (very good) to 5 (very poor).
[3]Means followed by a different letter are significantly different based on LSD (0.05).

TABLE 2

Mean performance of 'G12PR-63R2' and test strains in five Georgia trials in 2013.

| Strain | Seed yield (bu/a) | Maturity date | Plant height (in.) | Lodging rating[1] | Seed weight (mg/seed) | Seed quality (rating[2]) |
|---|---|---|---|---|---|---|
| G12PR-63R2 | 61.2a[3] | 10-17 | 35 | 1.5 | 139 | 1.4 |
| G00-3880 | 60.1a | 10-19 | 36 | 1.5 | 152 | 1.4 |
| AG7733 | 66.6b | 10-20 | 37 | 1.1 | 174 | 1.4 |
| P97M50 | 60.5a | 10-18 | 35 | 1.5 | 146 | 1.3 |
| AG7934 | 66.0b | 10-22 | 38 | 1.2 | 159 | 1.5 |

[1]Rating: 1 (all plants erect) to 5 (over 80% of plants prostrate).
[2]Rating: 1 (very good) to 5 (very poor).
[3]Means followed by a different letter are significantly different based on LSD (0.05).

TABLE 3

Mean performance of 'G12PR-63R2' and a test strain in five Southeast trials in 2013.

| Strain | Seed yield (bu/a) | Maturity date |
|---|---|---|
| G12PR-63R2 | 51.3a[1] | 10-25 |
| P97M50 | 48.8a | 10-26 |

[1]Means followed by a different letter are significantly different based on LSD (0.05).

TABLE 4

Mean performance of 'G12PR-63R2' and test strains in three North Carolina trials in 2013.

| Strain | Seed yield (bu/a) | Maturity date |
|---|---|---|
| G12PR-63R2 | 53.4a[1] | 10-26 |
| AG6931 | 53.6a | 10-24 |
| AG7231 | 52.5a | 10-24 |
| AG7733 | 55.0a | 10-28 |
| AG7934 | 56.0a | 10-30 |

[1]Means followed by a different letter are significantly different based on LSD (0.05).

EXAMPLE 3

'G12PR-63R2' Seed Yield

'G12PR-63R2' yielded 1.5 bu/a over the Roundup Ready® cultivar 'P97M50', but yielded 2.2 and 4.0 bu/a less than RR2Y commercial cultivars, 'AG7733' and 'AG7934', respectively (Table 5).

TABLE 5

Mean seed yield of 'G12PR-63R' and check cultivars across environments.

| Strain | 2012 PT (2)[1] bu/a | 2013 STV (5)[1] bu/a | 2013 PIO (5)[1] bu/a | 2013 MON (3)[1] bu/a | Mean (10)[1] bu/a | Mean (10)[1] bu/a | Mean (8)[1] bu/a | Mean (7)[1] bu/a |
|---|---|---|---|---|---|---|---|---|
| G12PR-63R2 | 62.7 | 61.2 | 51.3 | 53.4 | 59.2a[2] | 56.2a[2] | 58.3a[2] | 61.6ab[2] |
| AG7733 | 58.4 | 66.6 | — | 55.0 | 61.4a | — | 62.2b | 64.2a |
| AG7934 | — | 66.0 | — | 56.0 | — | — | 62.3b | — |
| P 97M50 | — | 60.5 | 48.8 | — | — | 54.7a | — | — |
| G00-3880[3] | 57.4 | 60.1 | — | — | — | — | — | 59.3b |

[1]Number of environments in each mean.
[2]Means followed by a different letter within a column are significantly different based on an LSD (0.10).
[3]Conventional (non-Roundup Ready) cultivar.

EXAMPLE 4

'G12PR-63R2' is Resistant to Nematodes

As shown in Table 6, 'G12PR-63R2' possesses resistance to SCN (R3), Southern, Peanut and Javanese root-knot nematode. 'G12PR-63R2' is adapted to areas of the southern USA (such as Georgia) that commonly grow MG VII soybean cultivars and to areas that are known to have or expected to have damaging levels of the Southern, Peanut, and Javanese root-knot nematodes and race 3 of soybean cyst nematode.

TABLE 6

Mean ratings for southern root-knot nematode, peanut root-knot nematode, Javanese root-knot nematode and reaction to two races of soybean cyst nematode of 'G12PR-63R2' and check cultivars.

|  |  | Root-knot nematode | | | Cyst nematode | |
|---|---|---|---|---|---|---|
| Company or Brand Name | Variety | Southern[1] rating[6] | Peanut[2] rating[6] | Javanese[3] rating[6] | Race 3[4] reaction[7] | Race 9[5] reaction[7] |
| UGA | G12PR-63R2 | 1.5 | 2.0 | 2.0 | R | S |
| UGA | G00-3880 | 2.0 | 2.0 | 3.0 | R | S |
| Asgrow | AG7733 | 2.3 | 4.8 | 4.8 | S | S |
| Pioneer | 97M50 | 1.0 | 4.5 | 5.0 | R | S |
| Check Variety | AGS Benning | 1.0 | 4.5 | 3.3 | R | S |
| Check Variety | Boggs | 1.0 | 2.5 | 1.5 | R | S |
| Check Variety | Bossier | 5.0 | 5.0 | 2.5 | S | S |
| Check Variety | CNS | 5.0 | 5.0 | 5.0 | S | S |
| Check Variety | G93-9009 | 1.0 | 1.0 | 1.0 | R | R |
| Check Variety | G93-9106 | 1.0 | 1.0 | 1.0 | R | R |
| Check Variety | GaSoy17 | 5.0 | 5.0 | 5.0 | S | S |
| Check Variety | Hagood | 2.3 | 5.0 | 4.8 | R | S |
| Check Variety | Hartwig | 1.8 | 4.3 | 3.8 | R | R |
| Check Variety | Haskell | 1.8 | 1.8 | 2.0 | S | S |
| Check Variety | Prichard | 1.0 | 4.8 | 5.0 | R | R |
|  | L.S.D.(0.10) | 0.7 | 0.7 | 0.6 |  |  |

[1]Meloidogyne incognita
[2]Meloidogyne arenaria
[3]Meloidogyne javanica
[4]The cyst indices on the differentials were: Peking = 0(−), Pickett = 0(−), PI88788 = 0(−), PI90763 = 0(−)
[5]The cyst indices on the differentials were: Peking = 48(+), Pickett = 90(+), PI88788 = 9(−), PI90763 = 8(−)
[6]Rating: 1 = (few galls) to 5 = (many galls).
[7]Reaction: R = Resistant (generally <10% of females or cysts per plant); MR = Moderate Resistance (generally 10 to 20% of females or cysts per plant); S = Susceptible (generally >20% of females or cysts per plant).

EXAMPLE 5

'G12PR-63R2' Protein and Oil Content

'G12PR-63R2' has similar protein (34%) and oil (18.8%) contents as its recurrent parent and check cultivars (Table 7).

TABLE 7

Protein and oil content of 'G12PR-63R' and check cultivars

| Strain | STV-OIL[1] (%) | STV-PRO (%) | CB-OIL[2,4] (%) | CB-PRO (%) | AVE-OIL[3] (%) | AVE-PRO (%) |
|---|---|---|---|---|---|---|
| G12PR-63R2 | 18.7 | 34.3 | 19.0 | 33.6 | 18.8 | 34.0 |
| G00-3880 | 19.2 | 33.9 | 19.5 | 33.6 | 19.3 | 33.8 |
| G00-3213 | 19.1 | 34.6 | 19.9 | 33.8 | 19.4 | 34.3 |
| P97M50 | 18.9 | 35.1 | — | — | — | — |
| AG7733 | 19.0 | 34.1 | — | — | — | — |
| AG7934 | 19.6 | 34.4 | — | — | — | — |
| Prichard | — | — | 19.4 | 32.6 | — | — |
| Boggs | — | — | 19.5 | 34.7 | — | — |

[1]STV = State Variety Test 471, Athens 2013
[2]CB = Crossing Block, Athens 2013
[3]AVE = Weighted means of CB (2 reps) and STV (3 reps)
[4]CB entry G12PR-6354 used CB Average in both 'G12PR-54R2' and 'G12PR-63R2'.

EXAMPLE 6

'G00-3880' Performance

'G00-3880', a recurrent parent of 'G12PR-63R2', was tested in over 30 locations across southeastern USA, and demonstrated high yield performance and adaptation (Table 8)

TABLE 8

Mean performance of recurrent parent 'G00-3880' and test varieties across 31 environments in Georgia and Southeast in 2004-2005.

| Strain | Seed yield (bu/a) | Maturity date | Plant height (in.) | Lodging rating[1] | Seed weight (mg/seed) | Seed quality rating[2] |
|---|---|---|---|---|---|---|
| G00-3880 | 46.7a[3] | 10-21 | 34 | 2.1 | 1.7 | 14.2 |
| Cook | 42.3b | 10-22 | 37 | 2.3 | 1.8 | 15.2 |
| Prichard RR | 37.2c | 10-22 | 38 | 2.8 | 1.8 | 13.0 |

[1]Rating: 1 (all plants erect) to 5 (over 80% of plants prostrate).
[2]Rating: 1 (very good) to 5 (very poor).
[3]Means followed by a different letter are significantly different based on LSD (0.05)

EXAMPLE 7

Production of 'G12PR-63R2' Soybeans

'G12PR-63R2' can be grown under normal conditions for growing soybeans, and bulk seed for large-scale planting can be obtained by methods known in certified seed production. For example, bulk seed may be produced by planting 'G12PR-63R2' seeds (such as those obtained from ATCC Accession No: PTA-122508), allowing the mature plants to produce seed by self-pollination with each other and then collecting the seed. Standard precautions should be taken to prevent cross-pollination from other soybeans, such as growing the variety in an isolated plot of sterilized soil, removing adjacent vegetation, etc. The 'G12PR-63R2' seeds deposited with ATCC are breeder seeds; propagation of plants from these seeds can be performed under standard conditions known to those skilled in the art.

EXAMPLE 8

Introducing Traits of 'G12PR-63R2' into Other Soybean Varieties

The morphological and physiological characteristics of 'G12PR-63R2', including resistance to many pests that affect soybeans (including Southern, Peanut, and Javanese root-knot nematode, and race 3 of soybean cyst nematode) as well as increased seed yield, can be introduced into other soybean varieties (such as other MG VII Roundup® Ready soybean cultivars) by conventional breeding techniques. For example, 'G12PR-63R2' can be grown in pollination proximity to another variety of soybean, allowing cross-pollination to occur between 'G12PR-63R2' and the other variety, and then harvesting the hybrid seeds. Plants grown from these hybrid seeds can then be tested for the maintenance of the characteristics described herein for 'G12PR-63R2' (such as one or more of resistance to Southern root-knot nematode, resistance to Peanut root-knot nematode, resistance to Javanese root-knot nematode, resistance to race 3 of soybean cyst nematode, and/or increased seed yield), and/or the plants can simply be observed to see if they display the same growth characteristics, seed yield, and pest resistance described in Tables 1-7.

For example, plants grown from these hybrid seeds can be tested for any of the morphological characteristics described herein, for improved seed yield, or for resistance to one or more of Southern root-knot nematode, Peanut root-knot nematode, Javanese root-knot nematode, and race 3 of soybean cyst nematode. In this way, resistance one or more of Javanese root-knot nematode, Southern root-knot nematode, Peanut root-knot nematode, race 3 of soybean cyst nematode, or increased seed yield may be combined with other desirable plant characteristics. Thus, the provision of 'G12PR-63R2' enables the production of progeny plants of 'G12PR-63R2' having resistance to one or more of Javanese root-knot nematode, Southern root-knot nematode, Peanut root-knot nematode, and race 3 of soybean cyst nematode, and in some examples resistance to all of these, and in some examples also improved seed yield. "Progeny plants" of 'G12PR-63R2' are any plants that are the offspring of a cross between 'G12PR-63R2' and any other plant or plants. Progeny plants also include successive generations of the offspring, for example those selected for resistance to one or more of Javanese root-knot nematode, Southern root-knot nematode, Peanut root-knot nematode, and race 3 of soybean cyst nematode, and in some examples resistance to all of these, and in some examples improved seed yield. First-generation progeny plants may retain the resistance to Javanese root-knot nematode, Southern root-knot nematode, Peanut root-knot nematode, and race 3 of soybean cyst nematode characteristics, as well as improved seed yield, of the 'G12PR-63R2' parent. However, if a first-generation progeny plant does not retain the desired level of resistance to Javanese root-knot nematode, Southern root-knot nematode, Peanut root-knot nematode, and race 3 of soybean cyst nematode, and in some examples also improved seed yield, observed with 'G12PR-63R2', subsequent generations of offspring can be recycled for resistance to these pests which have at least the same resistance to these pests as does 'G12PR-63R2' described herein. In one embodiment, subsequent generations of offspring can have resistance to Javanese root-knot nematode, Southern root-knot nematode, Peanut root-knot nematode, race 3 of soybean cyst nematode, and seed yield, similar to that or even that exceed that of 'G12PR-63R2'.

In addition, 'G12PR-63R2' can be used as transformation targets for the production of transgenic soybeans. In certain embodiments, the present disclosure contemplates the transformation of cells derived from 'G12PR-63R2' with at least one transgene. For example, transgenes that can be used, include, but are not limited to, transgenes that confer resistance to one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance; modified phosphorus characteristics; modified antioxidant characteristics; modified essential seed amino acid characteristics; modified fatty acid metabolism, modified carbohydrate metabolism, and modified soybean fiber characteristics. Examples of such genes and methods of transforming plants are described in U.S. Pat. No. 6,025,545.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A seed of soybean variety 'G12PR-63R2', wherein a representative sample of seed of said variety has been deposited under American Type Culture Collection (ATCC) Accession No. PTA-122508.

2. A seed mixture, comprising the seed of claim 1.

3. A soybean plant of soybean variety 'G12PR-63R2', wherein a representative sample of seed of soybean variety 'G12PR-63R2' has been deposited under ATCC Accession No. PTA-122508.

4. A plant part of the soybean plant of claim 3.

5. The plant part of claim 4, wherein the plant part is pollen, an ovule or a cell.

6. A tissue culture produced from protoplasts or cells from the soybean plant of claim 3.

7. The tissue culture of claim 6, wherein the cells or protoplasts are produced from a leaf, stem, protoplast, pollen, ovule, embryo, cotyledon, hypocotyl, meristematic cell, root, root tip, pistil, anther, flower, seed, shoot, stein, pod or petiole.

8. A soybean plant regenerated from the tissue culture of claim 7, wherein the soybean plant comprises all of the morphological and physiological characteristics of soybean variety 'G12PR-63R2', wherein a representative sample of seed of soybean variety 'G12PR-63R2' has been deposited under ATCC Accession No. PTA-122508.

9. A method of producing soybean seed, comprising:
 crossing the soybean plant of claim 3 with itself or a second soybean plant; and
 harvesting a resulting soybean seed.

10. The method of claim 9, wherein the second soybean plant is transgenic.

11. An $F_1$ hybrid seed produced by the method of claim 9.

12. A soybean plant, or a part thereof, produced by growing the seed of claim 11.

13. A method of producing a plant of soybean variety 'G12PR-63R2' comprising an added desired trait, wherein said method comprises the step of transforming a plant of soybean variety 'G12PR-63R2' with a transgene conferring the desired trait, thereby producing a plant of soybean variety 'G12PR-63R2' comprising the added desired trait, wherein a representative sample of seed of soybean variety 'G12PR-63R2' has been deposited under ATCC Accession No. PTA-122508.

14. The method of claim 13, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, modified fatty acid metabolism, modified carbohydrate metabolism, and modified soybean fiber characteristics.

15. The method of claim 13, wherein the transgene encodes phytase, fructosyltransferase, levansucrase, α-amylase, invertase, or an antisense of stearoyl-acyl carrier protein (ACP) desaturase.

16. The method of claim 14, wherein the resistance to an insect is conferred by a transgene encoding a *Bacillus thuringiensis* (Bt) endotoxin.

17. The method of claim 14, wherein the herbicide tolerance comprises tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, and chlorophenoxy acetic acid.

18. A plant produced by the method of claim 13, wherein said plant comprises the transgene conferring the desired trait and otherwise comprises all of the morphological and physiological characteristics of soybean variety 'G12PR-63R2'.

19. A method of introducing a desired trait into soybean variety 'G12PR-63R2' comprising:
(a) crossing a plant of variety 'G12PR-63R2' with a second plant comprising a desired trait to produce $F_1$ progeny plants wherein a representative sample of seed of soybean variety 'G12PR-63R2' has been deposited under ATCC Accession No. PTA-122508;
(b) selecting $F_1$ progeny plants that have the desired trait to produce selected $F_1$ progeny plants; (c) crossing the selected progeny plants with at least a first plant of variety 'G12PR-63R2' to produce backcross progeny plants;
(d) selecting backcross progeny plants that have the desired trait and physiological and morphological characteristics of soybean variety 'G12PR-63R2' to produce selected backcross progeny plants; and
(e) repeating steps (c) and (d) one or more times in succession to produce selected second or higher backcross progeny plants that comprise the desired trait and the physiological and morphological characteristics of soybean variety 'G12PR-63R2' when grown in the same environmental conditions.

20. The method of claim 19, wherein the desired trait comprises one or more of herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics, modified essential seed amino acid characteristics, modified fatty acid metabolism, modified carbohydrate metabolism, and modified soybean fiber characteristics.

21. A plant of soybean variety 'G12PR-63R2' further comprising a single locus conversion, wherein a representative sample of seed of soybean variety 'G12PR-63R2' has been deposited under ATCC Accession No. PTA-122508.

22. The plant of claim 21, wherein the single locus conversion is introduced into the plant by backcrossing or genetic transformation.

23. A soybean plant produced by transforming the soybean plant of claim 3 with a transgene that confers a desired trait, wherein the desired trait is one or more of herbicide tolerance, resistance to an insect, resistance to a bacterial disease, resistance to a viral disease, resistance to a fungal disease, resistance to a nematode, resistance to a pest, male sterility, site-specific recombination, abiotic stress tolerance, modified phosphorus characteristics, modified antioxidant characteristics, modified essential seed amino acid characteristics, modified fatty acid metabolism, modified carbohydrate metabolism, and modified soybean fiber characteristics.

24. A method of producing a hybrid soybean plant derived from soybean variety 'G12PR-63R2', comprising:
(a) preparing a progeny plant derived from soybean variety 'G12PR-63R2' by crossing a plant of the soybean variety 'G12PR-63R2' with a soybean plant of a second variety, wherein a representative sample of seed of soybean variety 'G12PR-63R2' has been deposited under ATCC Accession No. PTA-122508;
(b) crossing the progeny plant with itself or a second plant to produce a seed of a progeny plant of a subsequent generation;
(c) growing a progeny plant of a subsequent generation from said seed and crossing the progeny plant of a subsequent generation with itself or a second plant; and
(d) repeating steps (b) and (c) for an additional 3-10 generations with sufficient inbreeding to produce f4-bahybrid soybean plant derived from the soybean variety 'G12PR-63R2.

25. An $F_1$ plant produced by the method of claim 24.

26. A method of producing a commodity plant product comprising:
obtaining the soybean plant of claim 3 or a part thereof; and producing the commodity plant product therefrom.

27. The method of claim 26, wherein the commodity plant product is protein concentrate, protein isolate, soybean hulls, meal, flour or oil.

* * * * *